United States Patent [19]

Yanaihara et al.

[11] 4,064,235
[45] Dec. 20, 1977

[54] DOPAMINE DERIVATIVE COMPOUNDS, PREPARATION THEREOF AND MEDICINE CONTAINING SAME

[75] Inventors: Noboru Yanaihara, Shizuoka; Toshiji Igarashi, Tokorozawa; Youichi Kunii, Funabashi, all of Japan

[73] Assignee: Eisai Co., Ltd., Tokyo, Japan

[21] Appl. No.: 715,008

[22] Filed: Aug. 17, 1976

[30] Foreign Application Priority Data

Aug. 21, 1975 Japan .................................. 50-100623
Jan. 19, 1976 Japan .................................. 51-4022

[51] Int. Cl.$^2$ ..................... A61K 37/00; C07C 103/52
[52] U.S. Cl. ............................. 424/177; 260/112.5 R
[58] Field of Search .................. 424/177; 260/112.5 R

[56] References Cited

U.S. PATENT DOCUMENTS 3,803,120  4/1974  Felix ...................................... 424/177

OTHER PUBLICATIONS

Jones et al.; Am. Chem. Soc., 165, Meet. Medi. 11, 1973.
John L. McNay et al.; Chem. Abst. 63, 1965, p. 8916g.
Sandler et al.; Prog. Med. Chem. 6, 200, 1969.
D. B. Calne et al.; Nature 226, 1970, pp. 21-24.

*Primary Examiner*—Delbert R. Phillips
*Attorney, Agent, or Firm*—Blanchard, Flynn, Thiel, Boutell & Tanis

[57] ABSTRACT

A novel dopamine derivative compound having the following general formula and pharmacologically acceptable acid addition salt thereof:

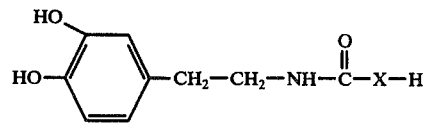

wherein X stands for a di- or tri-peptide residue derived from alanine, glycine, glutamine, isoleucine, lysine, leucine, tyrosine proline or valine, having an excellent activity of increasing the renal blood flow are provided.

14 Claims, No Drawings

DOPAMINE DERIVATIVE COMPOUNDS, PREPARATION THEREOF AND MEDICINE CONTAINING SAME

BACKGROUND OF THE INVENTION

1. FIELD OF THE INVENTION

The present invention relates to novel dopamine derivative compounds and medicines containing the same.

Further, this invention relates to a method of producing such novel compounds.

2. DESCRIPTION OF THE PRIOR ARTS

It is known that dopamine is different from other catechol amines in the point that dopamine has a specific activity of increasing the renal blood flow (John L. Mc'Nay et al, Circulation Research, vol. XVI, June 1965, pages 510 onward). Because of this specific activity, it has been considered to use dopamine for improving renal insufficiency accompanied by hyperpiesia or cardiac insufficiency and other similar diseases. However, since dopamine is promptly converted to norepinephrine or the like by metabolism and the activity is insufficient in duration, it has been difficult to put this compound into practical use. Accordingly, various research works have been made with a view to overcoming the above defect of dopamine, and it has recently been reported that N-L-isoleucyl dopamine, which is an aminoacid amide of dopamine, has an activity of increasing the renal blood flood, which is more durable than that of dopamine (Am. Chem. So., 165, Meet. MEDI. 11, 1973). As a result of the tracing experiment, it was found that the renal blood flow promoting activity of isoleucyl dopamine is low and the activity retention time must be further improved though the activity retention time of isoleucyl dopamine is longer than that of dopamine. We have made research works with a view to overcoming these defects involved in the known compounds and found that this object can be fully attained by novel compounds of the present invention.

SUMMARY OF THE INVENTION

According to the present invention, there is provided a novel dopamine derivative represented by the following general formula (I):

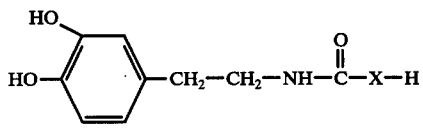

wherein X standas for a di- or tri-peptide residue derived from alanine, glycine, glutamine, isoleucine, lysine, leucine, tyrosine proline or valine.

More particulary, the invention relates to dopamine di- and tri-peptideamides, pharmacologically acceptable acid addition salts thereof and medicines containing these compounds.

By the term "pharmacologically acceptable acid addition salt" used herein is meant a non-toxic acid addition salt formed by reacting the novel compound of the present invention with a suitable organic or inorganic acid. For example, there can be mentioned hydrochlorides, hydrobromides, sulfates, bisulfates, acetates, oxalates, valates, oleates, laurates, butyrates, p-toluene-sulfonates, succinates and tartrates of the compounds represented by the above general formula (I). These compounds of the formula (I) and pharmacologically acceptable acid addition salts thereof have an excellent activity of increasing the renal blood flow.

As is apparent from results of the pharmacological experiment described hereinafter, each of the compounds of the present invention has a higher and more durable activity of increasing the renal blood flow than the above-mentioned known compound, isoleucyl dopamine.

Pharmacological Experiment

Test Item:
Measurement of the renal blood flow increasing activity. Compounds Tested:
1. N-L-Isoleucyl dopamine acetate (hereinafter referred to as "known compound A").
2. N-L-isoleucylvalyl dopamine acetate (hereinafter referred to as "compound A of the present invention").
3. N-Glycyl-L-glutamyl dopamine acetate (hereinafter referred to as "compound B of the present invention").
4. N-Glycyl-L-prolyl dopamine acetate (hereinafter referred to as "compound C of the present invention").
5. N-Glycylglycyl-L-leucyl dopamine acetate (hereinafter referred to as "compound D of the present invention").
6. N-Glycylglycyl-L-prolyl dopamine acetate (hereinafter referred to as "compound E of the present invention").

Animal Tested:
Crossbred adult dogs (irrespective of the sex) having a body weight of about 15 Kg were used.

Measurement Method:
The test animal was anesthetized by an intravenous injection of pentobarbital sodium salt (30 mg/Kg) and the abdominal region was fixed. The back region was opened and a probe of a rectangular wave electromagnetic flow meter (Model MF-26 manufactured by Nippon Koden K. K.) was attached to the artery of the left kidney to determine the renal blood flow rate (R. B. F.).

Each test compound was dissolved in distilled water and administered to the test animal from a vinyl resin fine tube inserted and fixed into the crotch vein. The amount administered was 1 mg/Kg/min. and the administration was conducted continuously over a period of 3 minutes.

The degree of increase of the renal blood flow rate by administration of the test compound was expressed in terms of the increase ratio (%), namely the ratio of the increase of the flow rate (when the flow rate was highest) to the flow rate before administration of the test compound. The duration of the activity was simultaneously examined.

Prior to the experiment, it was confirmed that, in the test animal, the renal blood flow rate was increased by administration of dopamine. Measurement Results:

With respect to each of the test compounds, it was found that the renal blood flow rate was increased by administration. Measurement results are shown in the following Table.

| Test Compound | Renal Blood Flow Rate Increase Ratio (%) | Duration Time of Activity (Minutes) |
|---|---|---|
| Compound A of Present Invention | 33 | 10 |

| Test Compound | Renal Blood Flow Rate Increase Ratio (%) | Duration Time of Activity (Minutes) |
|---|---|---|
| Compound B of Present Invention | 33 | 60 |
| Compound C of Present Invention | 30 | 60 |
| Compound D of Present Invention | 37 | 20 |
| Compound E of Present Invention | 36 | 30 |
| Known Compound A | 10 | 6 |

Conclusion:

As is apparent from the foregoing experimental results, it was found that all of the compounds tested have a renal blood flow increasing activity and the compounds A, B, C, D and E of the present invention are excellent over the known compound A with respect to the intensity of the activity and the activity duration.

From the results of the above pharmacological test, it is apparent that the compounds of the present invention exemplified by the foregoing compounds A, B, C, D and E of the present invention have a renal blood flow increasing activity 3 to 4 times as high as that of the known compound A and their activity duration is 2 to 10 times as high as that of the known compound A.

In view of the foregoing, it is expected that the compounds of the present invention will be very valuable for prevention and remedy of various diseases caused by renal blood flow troubles, such as renal hypertension, other hypertensions and congestive heart failure. Still further, it was found that the compounds of the present invention have an excellent pancreatic secretion increasing activity.

It is preferred that compounds of the formula (I) and pharmacologically acceptable acid addition salts thereof be administered in amounts of 10 to 500 mg per day of adults several times every day.

In the present invention, compounds of the formula (I) and pharmacologically acceptable salts thereof may be administered orally and non-orally according to customary methods in the form of injections, suppositories and the like. In the present invention, compounds of the formula (I) and pharmacologically acceptable acid addition salts thereof are administered as single substances or in preparations formed by combining them with suitable liquid or solid carriers having no adverse influences. For example, they may be administered in such preparations as tablets, granules, powders, capsules, buccal tablets, syrups, suspensions and injections. As the solid carrier that can be mixed with compounds of the formula (I) and pharmacologically acceptable acid addition salts thereof, there can be mentioned, for example, corn starch, lactose, talc, stearic acid, magnesium stearate and rubbery substances. As the liquid carrier that can be used for forming injections, suspensions and other liquid preparations, there can be mentioned, for example, water, vegetable oils, emulsifiers and surface active agents.

According to the present invention, compounds of the formula (I) can be synthesized by a method comprising removing a protective group from a protected dopamine derivative represented by the following general formula (II):

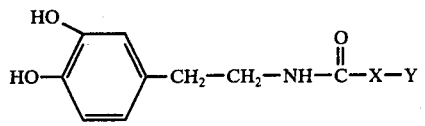

wherein X is as defined above and Y stands for an amino-protective group,
by a chemical treatment to thereby form a dopamine di- or tri-peptideamide represented by the following general formula (I):

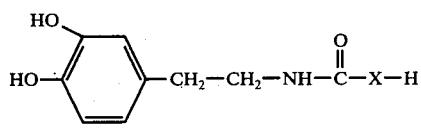

wherein X is as defined above.

Protective groups customarily used in the peptide synthesis chemistry are used as the amino-protective group Y in the above method of the present invention. For example, there can be mentioned acyl type protective groups such as formyl, benzoyl, phthalyl, trifluoroacetyl and tosyl groups, alkyl type protective groups such as toluyl, benzyl and alkylidene groups, and urethane type protective groups such as benzyloxycarbonyl, p-chlorobenzyloxycarbonyl, p-bromobenzyloxycarbonyl, p-methoxybenzyloxycarbonyl, tolyloxycarbonyl, cyclohexyloxycarbonyl and t-butoxycarbonyl groups. Removal of the protective group can be accomplished by known treatments such as trifluoroacetic acid treatment, hydrobromic acid treatment and catalytic reduction using a Pd-C catalyst or the like. For example, when the aminoprotective group is a benzyloxycarbonyl group, removal of the protective group can be accomplished by a catalytic reduction method using palladium-carbon as a catalytic reduction catalyst in a solvent such as methanol, ethanol, dioxane and dimethyl formamide or a hydrogen bromide method [see Bulletin of the Japanese Chemical Society, 40, 2164 (1967)]. When the protective group is a t-butoxycarbonyl group, the protective group can be removed by trifluoroacetic acid treatment.

Compounds of the formula (II) that are used for the synthesis of the compounds of the present invention are novel compounds. These compounds of the formula (II) can be obtained, for example, by reacting dopamine with a di- or tri-peptide represented by the following general formula (III):

wherein X and Y are as defined above,
according to a method customarily used for formation of a peptide linkage, for example, an azide method, a mixed acid anhydride method, a carbodiimide method or an active ester method. Relatively good results are obtained when the mixed acid anhydride method is adopted. In this condensation reaction, amide type solvents such as dimethyl formamide and dimethyl acetamide, halogenated alkyl type solvents such as dichloromethane, chloroform and carbon tetrachloride, and ether type solvents such as ethyl ether, tetrahydrofuran and dioxane may be used singly or in the form of a mixture of two or more of them.

The present invention will now be described in detail by reference to the following Examples, in which when amino acids used had an optical activity, L-isomers were employed and a 4:5:1 mixed solvent of n-butanol:-water:acetic acid was used as the developing solvent for silica gel thin layer chromatography.

EXAMPLE 1 (SYNTHESIS OF N-GLYCYLPROLYL DOPAMINE)

In 20 ml of tetrahydrofuran were dissolved 674 mg of carbobenzoxyglycylproline and 0.22 ml of N-methylmorpholine, and the solution was cooled to $-15°$ C. Then, 0.31 ml of isobutyl chloroformate was added to the solution and the mixture was added to 10 ml of a dimethyl formamide solution containing 0.28 ml of triethylamine, which was cooled to $-15°$ C. The mixture was agitated for 10 minutes at $0°$ C. and for another 10 minutes at $20°$ C. The solvent was distilled and the residue was dissolved in water-saturated 1-butanol, and the solution was washed with 1-butanol-saturated distilled water 5 times. The 1-butanol layer was collected, the solvent was distilled and the residue was solidified from ether. The resulting product was N-carbobenzoxyglycylprolyl dopamine.

The resulting solid product was added to 60 ml of methanol, and the catalytic reduction was conducted for 20 hours by using palladium-carbon as a catalytic reduction catalyst. After completion of the reaction, the catalyst was removed by filtration, and the solvent was distilled from the filtrate and the residue was dried under reduced pressure and dissolved in a small quanity of 1M acetic acid. Thus, gel filtration was conducted in a column (4.0 cm $\times$ 45 cm) packed with Bio Gel P-2 by using 1M acetic acid as an elution solvent. Fractions Nos. 38 to 43 (each fraction being 13 g) were collected, and the solvent was distilled from the mixture and the residue was subjected to freeze-drying in the presence of a small quantity of water to obtain 374 mg of a white powdery product, which was an acetate of the intended product. Elementary Analysis Values as $C_{15}H_{21}N_3O_4 \cdot CH_3COOH$:

Calculated: C = 55.57%, H = 6.86%, N = 11.44%
Found: C = 55.31%, H = 6.64%, N = 11.71% $[\alpha]_D^{19}$: $-69.0$ (C, 0.53, MeOH) Silica Gel Thin Layer Chromatogram: Rf = 0.39

EXAMPLE 2 (SYNTHESIS OF N-GLYCYLGLYCYLPROLYL DOPAMINE)

In the same manner as described in Example 1, 800 mg of carbobenzoxyglycylglycylproline and 380 mg of dopamine hydrochloride were reacted and treated to obtain N-carbobenzoxyglycylglycylprolyl dopamine. This compound was subjected to the catalytic reduction treatment in the same manner as described in Example 1. At the gel filtration, fractions Nos. 40 to 48 were collected. There was obtained 380 mg of a white powdery product, which was an acetate of the intended product. Elementary Analysis Values as $C_{17}H_{24}N_4O_5 \cdot CH_3COOH \cdot \frac{1}{2}H_2O$:

Calculated: C = 52.65%, H = 6.74%, N = 12.93%
Found: C = 52.17%, H = 6.14%, N = 13.25% $[\alpha]_D^{19}$: $-66.3$ (C, 1.06, MeOH) Thin Layer Chromatogram: Rf = 0.23

Other dopamine derivatives are shown in the following Table.

Compound (I)

$$\text{HO-}\bigcirc\text{-CH}_2\text{-CH}_2\text{-NH-}\overset{O}{\underset{\|}{C}}\text{-X-H} \qquad (1)$$

(with HO- also on the ring)

| Example No. | H—X—$\overset{O}{\underset{\|}{C}}$— | Molecular Formula | C | H | N | Other Measurement Values |
|---|---|---|---|---|---|---|
| 3 | H-Ala-Gln- | $C_{16}H_{24}N_2O_5 \cdot CH_3COOH \cdot H_2O$ | 50.23 / 50.40 | 7.03 / 6.77 | 13.02 / 12.74 | Rf = 0.39; $[\alpha]_D^{20} = -14.2$ (C, 1.02, MeOH) |
| 4 | H-Gly-Gln- | $C_{15}H_{22}N_4O_5 \cdot CH_3COOH$ | 51.25 / 51.75 | 6.58 / 6.38 | 14.06 / 14.01 | Rf = 0.26; $[\alpha]_D^{20} = -16.0$ (C, 1.03, MeOH) |
| 5 | H-Gly-Gly-Leu- | $C_{16}H_{28}N_4O_5 \cdot 1/2CH_3COOH$ | 55.59 / 55.32 | 7.36 / 7.11 | 13.65 / 14.00 | Rf = 0.57; $[\alpha]_D^{19} = -32.6$ (C, 0.63, MeOH) |
| 6 | H-Gly-Gly- | $C_{12}H_{17}N_3O_4 \cdot CH_3COOH \cdot H_2O$ | 48.69 / 48.56 | 6.72 / 6.97 | 12.17 / 12.27 | Rf = 0.41 |
| 7 | H-Gly-Gly-Val- | $C_{17}H_{26}N_4O_5 \cdot CH_3COOH \cdot 1/2H_2O$ | 52.40 / 52.44 | 7.17 / 7.44 | 12.87 / 12.79 | Rf = 0.62; $[\alpha]_D^{24} = -36.3$ (C, 0.52, MeOH) |
| 8 | H-Gly-Leu- | $C_{18}H_{28}N_3O_6 \cdot CH_3COOH$ | 56.53 / 56.23 | 7.38 / 7.89 | 10.99 / 11.27 | Rf = 0.70; $[\alpha]_D^{24} = -28.6$ (C, 0.65, MeOH) |
| 9 | H-Val-Ile- | $C_{19}H_{31}N_3O_4$ | 62.44 / 61.79 | 8.55 / 8.59 | 11.50 / 11.76 | Rf = 0.62; $[\alpha]_D^{24} = -25.5$ (C, 0.51, MeOH) |
| 10 | H-Gly-Tyr- | $C_{19}H_{23}N_3O_5 \cdot 1/2CH_3COOH$ | 59.53 / 59.14 | 6.25 / 6.00 | 10.42 / 10.57 | Rf = 0.60; $[\alpha]_D^{24} = +11.4$ (C, 0.53, MeOH) |
| 11 | H-Ile-Val- | $C_{19}H_{31}N_3O_4 \cdot CH_3COOH$ | 59.27 / 59.17 | 8.29 / 8.51 | 9.88 / 10.15 | Rf = 0.66; $[\alpha]_D^{24} = -29.4$ (C, 0.56, MeOH) |
| 12 | H-Gly-Lys- | $C_{16}H_{26}N_4O_4 \cdot 2CH_3COOH \cdot H_2O$ | 50.41 / 50.54 | 7.62 / 7.59 | 14.76 / 11.86 | Rf = 0.23; $[\alpha]_D^{24} = -10.3$ (C, 0.49, MeOH |
| 13 | H-Gly-Val-Ile- | $C_{21}H_{34}N_4O_5 \cdot CH_3COOH \cdot H_2O$ | 55.18 / 55.19 | 8.05 / 7.92 | 11.19 / 10.98 | Rf = 0.64; $[\alpha]_D^{24} = -44$ (C, 0.51, MeOH) |
| 14 | H-Gly-Val-Val- | $C_{20}H_{32}N_4O_5 \cdot CH_3COOH \cdot H_2O$ | 54.30 / 53.96 | 7.87 / 7.72 | 11.52 / 10.82 | Rf = 0.62; $[\alpha]_D^{24} = -52.9$ (C, 0.55, MeOH) |

EXAMPLE 15 (TABLET)

N-Glycylglycylleucyl dopamine hydrochloride: 150 g

Corn starch: 1500 g

Stearic acid: 25 g

Hydroxylpropyl cellulose: 25 g

By using the above composition, tablets, each of which contained 100 mg of N-glycylglycylleucyl dopamine hydrochloride, were prepared according to a customary method.

EXAMPLE 16 (INJECTION)

| | |
|---|---:|
| N-Glycylglycylleucyl dopamine hydrochloride | 50 g |
| Distilled water for injection | balance |
| Total | 10 l |

Ampoules (containing 2 ml of an injection and 10 mg of N-glycylglycylleucyl dopamine hydrochloride per ampoule) were prepared from the above composition according to a customary method. The isotonic treatment with biological sodium chloride solution and the high pressure sterilization treatment were conducted.

EXAMPLE 17 (LIQUID PREPARATION FOR ORAL ADMINISTRATION)

N-Glycylglycylleucyl dopamine hydrochloride: 5 g
Syrup base: 200 ml
Glycol: 200 ml
Ethyl p-hydroxybenzoate: 1 g
Orange essence: 0.5 ml A liquid preparation for oral administration was prepared from the above composition according to a customary method.

The embodiments of the invention in which an exclusive property or privilege is claimed are defined as follows:

1. A compound having the formula:

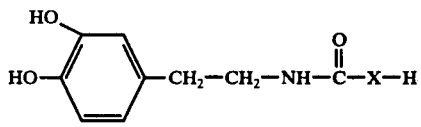

wherein X is a di- or tri-peptide residue derived from alanine, glycine, glutamine, isoleucine, lysine, leucine, tyrosine, proline or valine, or a pharmacologically acceptable acid addition salt thereof.

2. A compound as claimed in claim 1 wherein the group

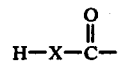

is a glycyl-L-prolyl group.

3. A compound as claimed in claim 1 wherein the group

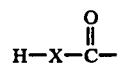

is a L-isoleucylvalyl group.

4. A compound as claimed in claim 1 wherein the group

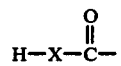

is a glycyl-L-glutamyl group.

5. A compound as claimed in claim 1 wherein the group

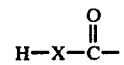

is a glycylglycyl-L-Leucyl group.

6. A compound as claimed in claim 1 wherein the group

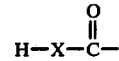

is a glycylglycyl-L-prolyl group.

7. A method of increasing the renal blood flow rate in a subject requiring such treament, which comprises: administering to such subject a therapeutically effective amount of a compound having the formula:

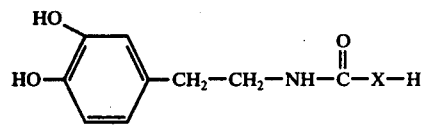

wherein X is a di- or tri-peptide residue derived from alanine, glycine, glutamine, isoleucine, lysine, leucine, tyrosine, proline or valine, or a pharmacologically acceptable acid addition salt thereof.

8. A method as claimed in claim 7 wherein the group

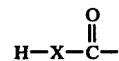

is a glycyl-L-prolyl group.

9. A method as claimed in claim 7 wherein the group

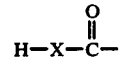

is an L-isoleucylvalyl group.

10. A method as claimed in claim 7 wherein the group

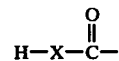

is a glycyl-L-glutamyl group.

11. A method as claimed in claim 7 wherein the group

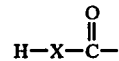

is a glycylglycyl-L-leucyl group.

12. A method as claimed in claim 7 wherein the group

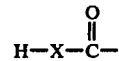

is a glycylglycyl-L-prolyl group.

13. A method according to claim 7 in which said compound is administered in combination with a pharmaceutical carrier.

14. A method according to claim 7 in which the compound is administered in an amount of from 10 to 500 mg per day.

* * * * *